United States Patent [19]

Steiner et al.

[11] Patent Number: 4,955,865
[45] Date of Patent: Sep. 11, 1990

[54] NEEDLE UNSHEATHING, RESHEATHING AND HANDLING APPARATUS

[75] Inventors: Eric L. Steiner, Denver; Arthur J. Sable, Boulder, both of Colo.

[73] Assignee: On-Gard Systems, Inc., Denver, Colo.

[21] Appl. No.: 298,619

[22] Filed: Jan. 18, 1989

[51] Int. Cl.5 ............................................. A61M 5/32
[52] U.S. Cl. .................................... 604/192; 604/263
[58] Field of Search ....................... 604/192, 263, 187

[56] References Cited

U.S. PATENT DOCUMENTS

| | | |
|---|---|---|
| 1,378,806 | 5/1921 | Ausubel . |
| 2,117,469 | 5/1938 | Woodyatt . |
| 3,107,785 | 10/1962 | Roehr . |
| 3,642,123 | 2/1972 | Knox . |
| 4,043,334 | 8/1977 | Brown et al. . |
| 4,062,353 | 12/1977 | Foster et al. . |
| 4,286,591 | 9/1981 | Raines . |
| 4,287,988 | 9/1981 | House . |
| 4,485,918 | 12/1984 | Mayer . |
| 4,573,975 | 3/1986 | Frist et al. . |
| 4,596,562 | 6/1986 | Vernon . |
| 4,717,386 | 1/1988 | Simmons . |
| 4,747,837 | 5/1988 | Hauck . |

FOREIGN PATENT DOCUMENTS

| | | | |
|---|---|---|---|
| 2586566 | 3/1987 | France | 604/192 |
| 2586568 | 3/1987 | France | 604/263 |
| 85/03006 | 7/1985 | World Int. Prop. O. | 604/192 |

Primary Examiner—John D. Yasko
Attorney, Agent, or Firm—Sheridan, Ross & McIntosh

[57] ABSTRACT

The present invention is principally directed to an apparatus for unsheathing, resheathing and handling needles. The preferred embodiment includes an elongated housing having an opening at one end that communicates with an internal chamber. Sheath retaining members are disposed substantially adjacent to the opening and can be employed for selective retaining engagement of a sheath that is inserted into the opening. The sheath retaining members may include a deflectable spring member. A gripping portion may be provided in connection with the housing. Appropriate use of the apparatus obviates the need for manual grasping of a needle sheath and provides additional advantages.

18 Claims, 4 Drawing Sheets

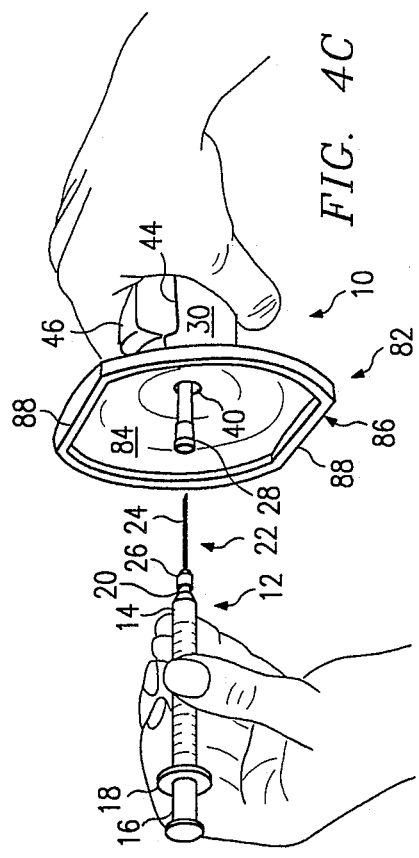
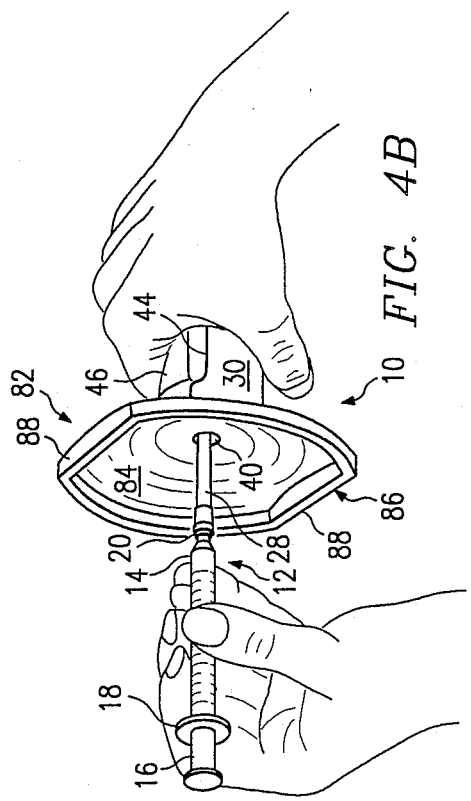
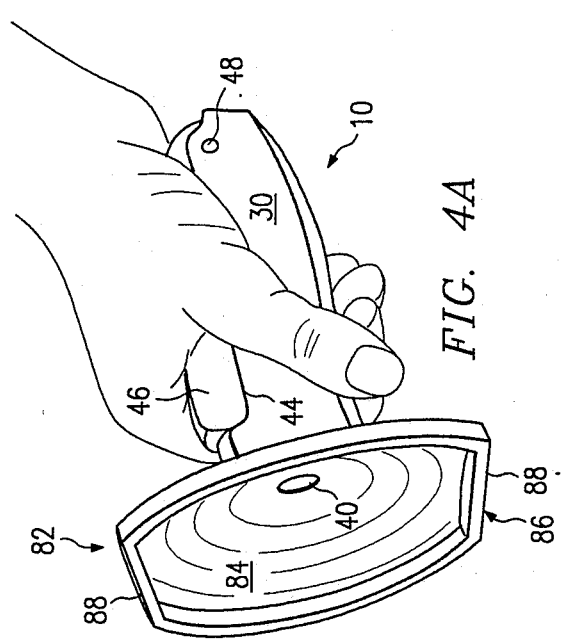

NEEDLE UNSHEATHING, RESHEATHING AND HANDLING APPARATUS

FIELD OF THE INVENTION

This invention relates to the unsheathing, resheathing and handling of needles, including without limitation syringe needles. More particularly, the present invention is directed to a safe and convenient apparatus for selectively engaging and retaining needle sheaths, for holding needles and syringes during periods of non-use in multiple applications, for sheathing needles after use, and for assisting in the disconnection of sheathed syringe needles from syringe bodies and the disposal thereof.

BACKGROUND OF THE INVENTION

Syringe needles are typically covered with protective sheaths prior to use, and it is desirable to resheath needles after use, including resheathing during multiple syringe use applications, and for needle disposal purposes. Consequently, the unsheathing, resheathing and disconnecting of sheathed needles from syringe bodies are procedures which are repeatedly carried out by doctors, nurses, technicians and the like.

As readily appreciated by such individuals, the above-noted procedures can become tedious and raise cross-contamination concerns, particularly when manual grasping of a sheath is required. Additionally, such procedures can result in "needle sticks", i.e., the inadvertent pricking of a hand. For example, needle sticks can occur when, during manual resheathing, a syringe needle misses the relatively small opening of a sheath and pricks the hand in which the sheath is being grasped. While a needle stick does not initially give rise to serious injury, the threat of communicating serious diseases, such as hepatitis and AIDS, is of great concern.

Various approaches have been proposed to address the above-noted problems. For example, syringes have been developed which include a telescoping shield member that can be selectively pulled over a syringe needle after use. Another new syringe includes a needle that can be retracted into the syringe body after use. These products are prohibitively expensive for most applications, and have proven to be subject to leakage and other contamination problems.

Of particular importance, a number of independent apparatus for assisting in syringe needle unsheathing, resheathing and disposal have been proposed. For example, U.S. Pat. No. 4,485,918 to Mayer, discloses a funnel-shaped apparatus, adapted to be hand-held by the tubular portion thereof. The tubular portion has a closed-end and is of a limited length so that, if the apparatus is held upright, a sheath can be supported within the apparatus and reapplied to a syringe needle. In addition to the inconvenience associated with the required upward orientation for sheath support and resheathing, it should be noted that the above-described Mayer apparatus does not include any features for selective removal of a sheath from a syringe needle.

Mayer further discloses a separate apparatus for assisting in resheathing and in the disconnection of a sheathed needle from a syringe body and the disposal thereof. Specifically, Mayer shows a box-shaped apparatus having an aperture in the ceiling with radially extending slots. In use, Mayer proposes that a sheath can be manually inserted into the aperture and supported about its flange by the adjacent ceiling portion. A needle can then be inserted into the sheath until resheathing is achieved. Mayer further proposes that a sheathed needle assembly can be pressed through the aperture due to ceiling flex permitted by the slots, moved laterally to cause abutting engagement between the needle hub and the adjacent ceiling portion, and that the syringe body can thereafter be pulled, and if necessary, twisted upward to cause disconnection of the needle assembly from the syringe body. It should be noted that this apparatus is not adapted to be handheld and fails to disclose any features for selective removal of a sheath from a needle. In addition, the aperture/slot arrangement of the apparatus would seem to accommodate only certain sizes of sheaths for successful resheathing and disposal, and would appear to be particularly subject to wear. Further, the apparatus requires either mechanical anchoring or manual holding during needle disconnection procedures.

U.S. Pat. No. 4,596,562 to Vernon, and U.S. Pat. No. 4,717,386 to Simmons, both disclose apparatus for assisting in the unsheathing, resheathing and/or handling of syringe needles wherein means for retaining engagement of a sheath are employed. In particular, the Vernon and Simmons apparatus each require forcible entry of a sheath into a restricted opening to effectuate sheath engagement and retention by the periphery of the opening.

For example, Vernon discloses a generally planar apparatus having at least one hole therethrough of a diameter corresponding to a diameter found along the length of typical tapered sheaths. Vernon also contemplates the provision of a slot at the top end of the disclosed apparatus, defined by two parallel, spaced plates, with a pie-shaped opening extending downward from one of the plates to accommodate access to the slot. Vernon proposes that, at least for resheathing, a sheath can be forced into either the opening or the slot until restrictive engagement between the outer periphery of the sheath and the periphery of the opening or slot occurs. A syringe needle can then be inserted into the supported sheath until resheathing is achieved, and subsequently removed from the apparatus by manual grasping and pulling of the sheath to cause disengagement. It is important to appreciate that such a procedure necessitates the initial inward positioning of a sheath to a specific location within an opening to effectuate retention, and the application of opposing forces to achieve both sheath engagement and disengagement. Such requirements present particular operational problems when the apparatus is to be handheld. Further, significant cross-contamination can occur between a sheath and a user's hand or glove during manual disengagement of a sheath from the Vernon apparatus. Finally, the contemplated handle of the Vernon apparatus is spatially removed from the proposed sheath retaining means, thereby contributing to needle/sheath alignment difficulties associated with resheathing.

In the disclosed Simmons apparatus, a cylindrical member with converging inner walls extends laterally away from a plate-like member. Simmons proposes that by forcing a sheath into the opening of the cylindrical member of the apparatus, restrictive engagement between the inner walls of the member and the periphery of the sheath can be achieved. Upon consideration, it is apparent that, as with the Vernon apparatus, initial sheath engagement necessitates specific sheath positioning and the provision of opposing forces. In addition, disengagement of a sheathed needle from the Simmons apparatus would entail the inconvenient grasping of a sheath by a user and could result in undesired cross-contamination. Further, it would seem that the sheath retaining means of the Simmons apparatus is particularly subject to significant wear as the result of the repetitive rubbing of sheaths against the inner-walls of the cylindrical member.

In view of the disadvantages corresponding with the above-noted, representative apparatus, it is apparent that a substantial need exists for a safe and convenient apparatus for assisting in initial needle unsheathing, sheath retention, syringe holding, needle resheathing, and sheathed needle disconnection and disposal procedures. Such an apparatus is singularly provided by the novel features incorporated into the present invention.

SUMMARY OF THE INVENTION

The present invention comprises a housing having an opening at one end that communicates with an internal chamber. The opening and chamber are adapted to receive typical needle sheaths. A sheath retaining means is disposed within the housing chamber substantially adjacent to the opening and can be selectively actuated by a user to engage a sheath that is inserted into the opening.

In one aspect of the present invention, the sheath retaining means may include a spring means and an actuator means that can be selectively operated by a user to mechanically effectuate desired movement of the spring means laterally away from and back towards the longitudinal center axis that passes through the housing opening. A seat member having at least one and preferably two-spaced V-shaped supports can be provided in an operative opposing relationship to the spring means within the housing so that a sheath inserted into the housing opening can be selectively and securely retained between the seat member and spring member. The spring means may be configured and disposed within the housing so that it is in deflected state with a portion thereof bearing against the seat member during periods of non-use. An uneven edge may also be provided on the spring member to contribute to effective sheath retention.

In a further aspect of the present invention, the housing portion that is substantially adjacent to the opening and surrounds a corresponding portion of the internal chamber is adapted to be gripped by the hand of a user. Additionally, a portion of the actuator means can be longitudinally disposed within such gripping portion. Further, a shield can be provided adjacent to the gripping portion and may extend laterally away from the housing opening.

Due to its novel design, as further described hereinbelow, the present invention yields various combined advantages with respect to unsheathing, sheath retention, sheathed needle-syringe holding, resheathing and sheathed needle disconnection and disposal.

For example, the retaining means of the present invention permits a sheath to be selectively engaged and retained when the same is located at any position along a continuum of positions relative to the retaining means. That is, there is no requirement that the sheath be positioned at any single location to effectuate a retaining engagement. Rather a range of positions, as substantially defined by the length of a sheath, are acceptable to effectuate engaging retention.

With further respect to the retaining means of the present invention, it should be appreciated that no forcible entry of a sheath within a restricted opening or forcible exit therefrom is required to effectuate retaining engagement or to effectuate disengagement. Stated differently, a user need not apply opposing push/pull forces to achieve retaining engagement or disengagement with the present invention.

Relatedly, it is important to realize that the preferred retaining means of the present invention is relatively easy to actuate. In particular, a non-linear cantilever spring can be pivotally mounted within a rearward portion of the housing and linearly disposed upon assembly. By virtue of such linear disposition, the cantilever spring is in a deflected, biased state during periods of non-use, and further biasing of the spring to effectuate sheath engagement or disengagement requires the application of only minimal forces by the user. That is, the preferred spring means exhibits a low actuation force to deflection ratio. Further, it should be noted that, when actuated to retainingly engage a sheath, the retaining means of the present invention equally restricts movement of a sheath in either direction relative to the retaining means. This is particularly important when unsheathing and resheathing procedures are considered.

Specifically, the retaining means of the present invention permits a user to unsheath and resheath a syringe needle inserted in the housing opening, and to remove a resheathed needle, without grasping or otherwise contacting the sheath with a user's hand. Since the present invention does not require such contact, convenience is maximized and attendant needlestick and cross-contamination concerns are significantly reduced, thereby making the present invention particularly apt for use in surgical applications and in multiple syringe use applications.

In the latter regard, the elongated housing of the present invention provides an effective counter-weight when the apparatus is used to hold a syringe during periods of non-use in multiple applications. Further, and as further described below, flat edges can be provided on the shield of the inventive apparatus to prevent rolling when the apparatus is placed upon a relatively flat surface, and the diameter of the shield can be selected so that the apparatus will have a desired upward orientation when the apparatus is placed upon a relatively flat surface. These features enhance use of the apparatus for holding syringes during periods of nonuse, and allow for convenient grasping of the apparatus for unsheathing, resheathing and other procedures.

In addition to the foregoing, the likelihood of needlestick is further minimized by the provision of the laterally extending shield. Additionally, convenient insertion of a sheathed or unsheathed syringe needle into the housing opening and sheath engagement and/or disengagement is provided by the present invention due to the spatial arrangement between the housing opening, the internal chamber thereof and the gripping portion of the housing. That is, the present invention provides an apparatus wherein insertion and sheath engagement and/or disengagement does not occur at a location spatially removed from the hand of a user. In a preferred embodiment of the invention, convenient insertion is further realized by providing a shield that is frusto-conically shaped to receive and direct a sheathed or unsheathed needle into the housing opening.

The inventive apparatus also advantageously provides an actuator member that can be conveniently operated by the palm or fingers of a user. This permits the apparatus to be utilized by those having small hands or a relatively weak grip.

Finally, it should be appreciated that the present invention further provides for a safe and convenient method of disconnection of a sheathed needle from a corresponding syringe body and for safe disposal thereof. Such advantages are provided since, as noted above, the retaining means of the present invention restricts movement of a sheath in either direction relative to the retaining means. More particularly, after resheathing has occurred, a user may pull, and if necessary, twist a syringe body away from the apparatus to effectuate disconnection of the syringe body from the sheathed needle assembly. Thereafter, the apparatus holding the sheathed needle can be carried to an appropriate disposal receptacle and the actuator member can be depressed to drop the sheathed needle in the receptacle. As should be appreciated, disconnection and disposal can therefore be accomplished without contact between a user's hand and a sheath or needle assembly.

DESCRIPTION OF THE DRAWINGS

FIGS. 4A–4C illustrate use of one embodiment of the present invention.

DESCRIPTION OF THE PREFERRED EMBODIMENT

Figure 1:
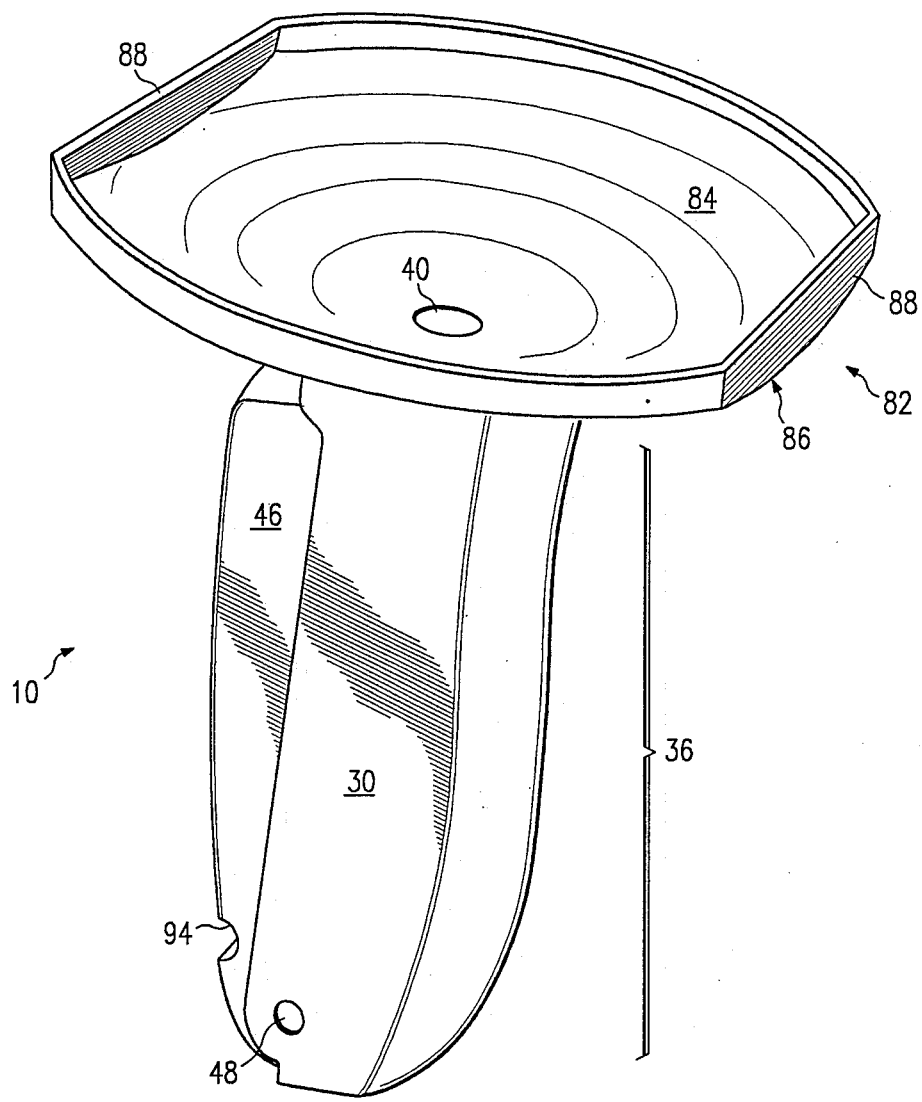
FIG. 1 is an elevated, perspective view of the preferred embodiment of the present invention.

For purposes of description herein, the terms "upper," "lower," "right," "left," "rear," "front," "vertical," "horizontal" and derivatives thereof shall relate to the invention as oriented in the preferred embodiments as exemplified in the drawings herein. However, it is to be understood that the invention may assume various alternative orientations and step sequences, except where expressly specified to the contrary. It is also to be understood that the specific devices and processes illustrated in the attached drawings, and described in the following specification, are only exemplary of the inventive concepts addressed in the appended claims. Hence, specific dimensions, physical characteristics, and procedures relating to the embodiments disclosed herein are not to be considered as limiting, unless the claims by their language expressly state otherwise.

The reference numeral 10 (FIGS. 1 and 2) generally designates a preferred embodiment of an apparatus embodying the present invention. The apparatus 10 is particularly adapted for use with syringes, such as the syringe 12 illustrated in FIGS. 4B and 4C. As is conventional, syringe 12 includes a chamber 14, a plunger 16, and has a flange 18 on one end. On the other end of syringe 12 is a spigot 20 for receiving a needle assembly 22 thereon. Needle assembly 22, which includes a needle 24 and hub 26 is typically press or threadingly fitted onto spigot 20, and covered by sheath 28 when syringe 12 is not in use.

The preferred embodiment 10 (Figs. 1 and 2) includes a housing 30 having a snap fitting 32, screw fitting 33 and defining recess 34. Housing 30 is an elongate shell constructed of injection-molded plastic, having a length of approximately 4.8 inches. As will be appreciated by those skilled in the art, the housing 30 and other components of the preferred embodiment 10 may be constructed of appropriate materials to permit sterilization within typical autoclaves.

Housing 30 defines a gripping section 36 along its outer surface (FIG. 2), adapted to be held by a user's hand (FIG. 4), and an internal chamber 38 therewithin. A sheath receiving aperture 40 (FIGS. 2 and 3), which communicates with internal chamber 38, is disposed at a front end of housing 30. In the present example, sheath receiving aperture 40 has a diameter of approximately 0.4 inches, thus providing an opening with an area great enough to receive all typically employed sheath sizes. More specifically, sheath 28 can be easily passed through sheath receiving aperture 40, without being hindered thereby. A sheath retrieving aperture 42, communicating with internal chamber 38, is disposed toward the rear of housing 30.

An aperture 44 (FIG. 2) is defined within gripping portion 36 and receives an actuator 46. While aperture 44 and actuator 46 are shown in a bottom portion of the preferred embodiment 10 in FIGS. 1–3, it should be understood that aperture 44 and actuator 46 could also be disposed in a top portion, as illustrated in FIGS. 4A–C.

One end of actuator 46 is pivotally connected with a rear section of housing 30 through use of a pivot pin 48. In the present example, the connection between actuator 46 and housing 30 is similar in design to that of a conventional stapler. An end of actuator 46, disposed opposite to the pivoted end, engages a cantilever spring 50.

Figure 2:
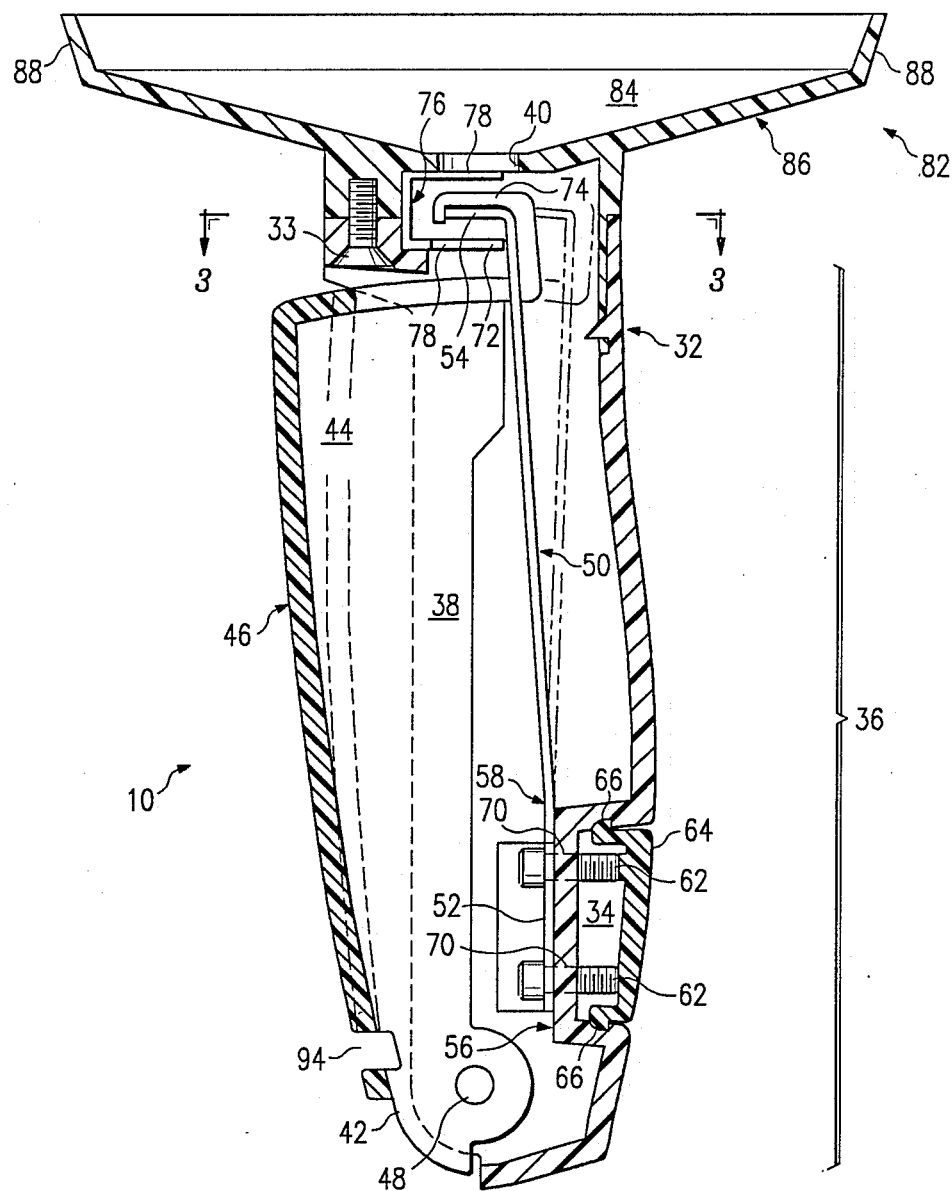
FIG. 2 is a cross-sectional, side view at the longitudinal center axis of the preferred embodiment of the present invention.

Cantilever spring 50 has a first end 52 and a second end 54. A first seat 56 of housing 30 is employed with screws 62 to secure first end 52 of cantilever spring 50 to housing 30. Screws 62 pass through apertures 70 in the first seat 56 and apertures (not shown) in the first end 52 of the cantilever spring 50. As will be appreciated by those skilled in the art, spring first end 52 could also be secured to housing 30 by way of conventional rivets. As illustrated in FIG. 2, a cover plate 64 is snap-fitted over recess 34 by nubs 66 so that recess 34 is sealed off during operation of the apparatus 10.

In the preferred embodiment 10, cantilever spring 50 can be fabricated from stainless steel and configured so that, prior to assembly of device 10, cantilever spring 50 is non-linear. In particular, in relation to FIG. 2, second end 54 may be disposed downward relative to first end 52 prior to assembly. Upon assembly as shown in FIG. 2, second end 54 will thus be in a deflected (i.e., biased) state, bearing downwardly against portion 72 of support seat 76. As a result of this arrangement, second end 54 of cantilever spring 50 can be further deflected by the application of minimal actuation forces, as will be further discussed.

Figure 3:
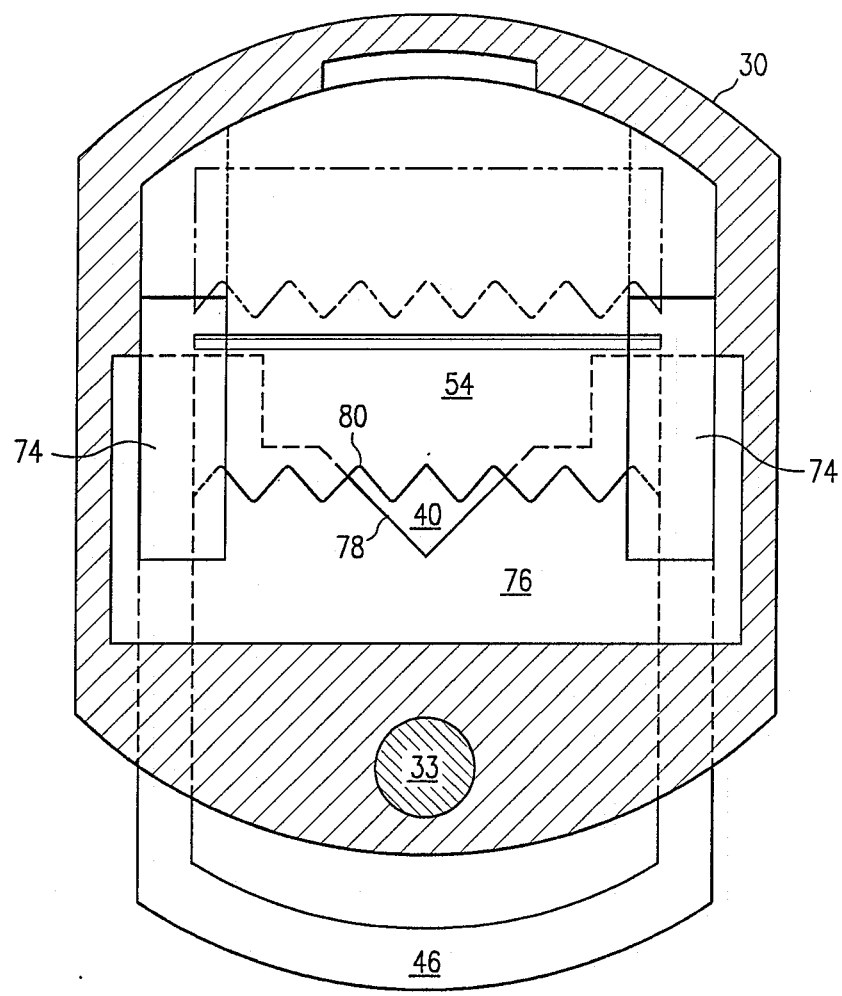
FIG. 3 is a cross-sectional end view of the preferred embodiment of the present invention, at plane 3—3 shown in FIG. 2.

As noted above, second spring end 54 engages the front end of actuator 46. In the present example, the front end of actuator 46, constituting two "ear" portions 74 (FIGS. 2 and 3), engages the outer edges of second end 54 of cantilever spring 50. A second seat 76 is operatively mounted within housing 30 near sheath receiving aperture 40 (FIGS. 2 and 3). When the preferred embodiment 10 is not in use, the aforementioned pre-stressing of spring 50 causes spring second end 54 to engage portion 72 of second seat 76. As shown in FIG.

3 access through sheath receiving aperture 40 is blocked during non-use of the preferred embodiment 10.

In order to freely insert sheath 28 through aperture 40 and into chamber 38 it is only necessary to depress actuator 46 such that second spring end 54 is displaced away from second seat 76. The design of actuator 46 facilitates convenient use thereof. More particularly, since actuator 46 is elongate it is easy to engage with the typical palm of a hand, and a considerable force can thereby be readily brought to bear on a surface thereof.

Sheath 28 can thus be retained between second end 54 of cantilever spring 50, and second seat 76. Second seat 76 (FIG. 3), in the preferred embodiment includes two support portions 78 each having a "V" shaped configuration for providing firm support along portions of retained sheath 28. As should be appreciated, second seat 76 serves the dual function of engaging the front end of actuator 46 when apparatus 10 is not in use, and contributing to sheath 28 retention when device 10 is being used for unsheathing, syringe holding or resheathing. Securement of sheath 28 within chamber 38 may be further facilitated by providing second end 54 of cantilever spring 50 with an uneven edge 80 (e.g., rounded serrations). Use of uneven edge 80 (FIG. 3) minimizes slipping of sheath 28 when spring second end 54 bears against a portion of the same.

Use of cantilever spring 50 greatly enhances the ability of device 10 to retain typically employed sheaths. More specifically, experimentation has found that an actuation force of no more than approximately 8 pounds need be applied to actuator 46 to deflect cantilever spring 50 for insertion of sheath 28, and that upon releasing spring 50 an average sheath retention force of approximately 5 pounds can be achieved. That is, the ratio of change in force, i.e., change in actuation force and retention force, to change in spring 50 deflection is relatively low. This is due to the preferred initial nonlinear configuration of cantilever spring 50 and the substantially linear disposition thereof in device 10, as described hereinabove. It should therefore be appreciated that through employment of cantilever spring 50, optimal sheath retention is achieved while minimizing the required actuation force. It should also be noted that the average sheath retention force of 5 pounds was selected to optimize retention of a typical sheath 28 during selective disengagement thereof from hub 26 during unsheathing, yet prevent distortion of sheath 28 during periods in which it is disposed between cantilever spring 50 and second seat 76. It should be further noted that a retention force of 5 pounds provides adequate support for selective disconnection of needle assembly 22 from spigot 20, as discussed in further detail below.

Surrounding sheath receiving aperture 40 is a shield 82. As best illustrated in FIG. 2, shield 82 is connected to housing 30 through use of snap fitting 32 and screw fitting 33 in the preferred embodiment. Shield 82 extends away from aperture 40 and is frusto-conically shaped. Surface 84 of shield 82 provides an area large enough to protect the hand (e.g., a diameter of approximately 4.6 inches) and serves to direct needle 24 toward receiving aperture 40 during use. Surface 84 has a perimeter edge 86 which includes angled edge portions 88. In the preferred embodiment, each of angled edge portions 88 are provided at approximately 17.5 degrees with respect to the longitudinal center axis of device 10. Consequently, apparatus 10 is inclined upward when placed on a flat surface. While in this position, apparatus 10 is capable of either holding sheath 28 alone or a sheath covered needle of syringe 12. As will be appreciated, the 17.5 degree angulation disposes apparatus 10 for easy insertion of syringe 12. Additionally, when device 10 is being used as a holder for syringe 12, the 17.5 degree angulation provides adequate clearance for plunger 16 and flange 18 with respect to the flat surface. Finally when housing 30 is resting on a flat surface at a 17.5 degree inclination, a space is provided between housing 30 and shield 82 so that gripping portion 36 can be easily grasped by the user.

An aperture 94 is disposed in housing 30 to facilitate securement of device 10 to a belt, hook or the like. That is, a strap or chain may be fed through aperture 94 so that device 10 can be hung or secured during periods in which device 10 is not being used.

To remove sheath 28 (FIGS. 4A-C) from syringe 12 using device 10, gripping portion 36 of housing 30 is grasped in the palm of the hand. Actuator 46 is depressed (FIG. 4B) so that the front end of actuator 46 deflects spring second end 54 away from second seat 76 to define an open passageway between sheath receiving aperture 40 and internal chamber 38. The sheathed needle of syringe 12 is then inserted through aperture 40 (FIGS. 4B and 4C) until a desired length of sheath 28 is contained within internal chamber 38. As will be appreciated by those skilled in the art the positioning of sheath 28 within chamber 38 is not critical as long as substantially any location disposed along the length of sheath 28 is positioned between spring second end 54 and supports 78 of second seat 76. It should be appreciated that if sheath 28 is accidently inserted past spring second end 54, it may be easily retrieved via aperture 42. Upon positioning sheath 28 accordingly, pressure is released from actuator 46, thus causing cantilever spring second end 54 to bear against sheath 28 and securing supports 78 against sheath 28 such that sheath 28 is held firmly in place. Syringe 12 is then pulled away, and the retaining force of spring 50 facilitates the separation of sheath 28 from syringe spigot 20. Upon unsheathing, there is no need for the user to continue holding device 10, so the same is typically placed on a flat surface until resheathing is desired.

The resheathing process is initiated by grasping gripping portion 36 in the palm and inserting needle 24 into sheath 28 until sheath 28 is press fitted against hub 26. Once needle assembly 22 is adequately inserted into sheath 28, actuator 46 is depressed so that spring second end 54 is directed away from a corresponding portion of sheath 28 and the same is effectively disengaged. Syringe 12 is then removed from device 10 and actuator 46 is released such that the front of actuator 46 and spring second end 54 again engages second seat 76, and receiving aperture 40 is blocked off.

It should be appreciated that apparatus 10 can be advantageously used as a holder for syringe 12. For example, rather than removing syringe 12 from device 10 after initially inserting syringe 12 and releasing actuator 46, it is possible, and often desirable, to simply place the device 10, with sheath covered needle 24 of syringe 12 therein, down on a flat surface until use of the syringe is desired. Similarly, rather than depressing actuator 46 and pulling syringe 12 away after inserting needle assembly 22 into secured sheath 28 for resheathing, it may be desirable to simply set device 10, with sheath covered needle 24 of syringe 12 therein, down on the flat surface until further use is desired. This procedure is particularly apt for multiple syringe use applications.

Due to its construction, apparatus 10 is advantageously suited for disconnection of needle assembly 22 and use with any appropriate disposal receptacle. Disposal of needle assembly 22 along with sheath 28 may be performed anytime after completing the resheathing process. For disconnection, syringe 12 is grasped along a section thereof, possibly at flange 18, and pulled away from the apparatus 10, while if necessary, slightly twisting syringe 12. As noted above, due to the 5 pounds retention force applied to sheath 28 in the preferred embodiment 10, the sheath 28 and needle assembly 22 are both firmly retained during the disconnection step. Subsequent to disconnection, apparatus 10, with sheath covered needle assembly 22 retained thereby, can be positioned over the disposal receptacle such that when actuator 46 is depressed, sheath 28 is disengaged and sheath covered needle assembly 22 falls into the receptacle. As should be appreciated, during the above-described disconnection and disposal processes the fingers do not touch the potentially contaminated needle assembly 22 or sheath 28. Thus, the possibility of undesired cross-contamination is minimized and convenience is served.

From the foregoing description, it will be appreciated by those skilled in the art that modifications or improvements may be made to the preferred embodiments disclosed herein without departing from the concepts disclosed. The scope of protection afforded is to be determined by the claims which follow and the breadth of interpretation that the law allows.

What is claimed is:

1. An apparatus for selectively retaining a needle sheath comprising:
   a housing;
   a gripping portion at least partially defined by said housing and adapted to be gripped by the hand of a user; and
   retaining means positioned at least partially within said housing and comprising an external portion that partially defines said griping portion and that is of a longitudinal length sufficient to allow at least the majority of a user's hand to apply pressure thereto for selectively engaging and disengaging a sheath when said gripping portion is gripped transversely by the user.

2. The apparatus of claim 1, further comprising:
   a first opening at a first end of said housing adapted to receive said sheath;
   an internal chamber within said housing and communicating with said first opening; and,
   wherein said external portion of said retaining means is defined by a controlling member, and said retaining means further comprises a separate, substantially shielded resilient means in movable contact with said controlling member and positioned to engage and retain said sheath adjacent to said first opening within said internal chamber during use.

3. An apparatus for selectively retaining a needle sheath comprising:
   a housing;
   a gripping portion at least partially defined by said housing and adapted to be gripped by the hand of a user;
   retaining means positioned at least partially within said housing for selectively engaging and retaining the sheath; and
   controlling means for permitting the user to selectively control engagement between said retaining means and said sheath, said controlling means partially defining said gripping portion and said controlling member being pivotally interconnected with said housing at one end of said housing.

4. The apparatus of claim 2, further comprising a second opening at a second end of said housing and communicating with said internal chamber.

5. An apparatus for selectively retaining a needle sheath comprising:
   a housing;
   a gripping portion adjacent to be gripped by the hand of a user;
   an opening at one end of said housing adapted to receive said sheath; and
   a shield extending laterally away form said opening and having at least one flat peripheral edge portion to restrict rotational movement of the apparatus when placed upon a support surface, wherein said one flat peripheral edge portion lies in a plane that transverses the longitudinal center axis of the apparatus rearward of said opening.

6. The apparatus of claim 5, wherein said shield is frusto-conical.

7. An apparatus for selectively retaining a needle sheath comprising:
   housing means; and
   resilient means interconnected with said housing means for selectively retaining a sheath by transversely engaging a limited sidewall portion of said sheath, wherein said engagement is limited to a plane that transverses the longitudinal center axis of the sheath; and,
   controlling means operatively associated with said resilient means for permitting a user to selectively control retaining engagement and disengagement of said resilient means and said sheath by applying pressure to said controlling means to deflect said resilient means, wherein the length of said controlling means is greater than the length of said limited sidewall portion and wherein sheath retention forces imparted by said resilient means are concentrated to said limited portion to restrict longitudinal, lateral and rotational movement of said sheath during use of the apparatus.

8. The apparatus of claim 7 wherein said resilient means comprises a spring means having a surface particularly adapted for restrictingly engaging said sheath.

9. The apparatus of claim 8, wherein an edge portion of said spring means engages said sheath and wherein said edge portion includes two or more projections.

10. The apparatus of claim 8 wherein said spring means is elongated and includes an end which is interconnected with said housing in a cantilever manner about an axis substantially parallel to the longitudinal center axis of the apparatus.

11. The apparatus of claim 10, wherein said elongated spring means has a non-linear shape prior to assembly of the apparatus, wherein upon assembly of the apparatus one end of said cantilever spring is deflected in a first direction to a first position, and wherein during operation of the apparatus said one end of said cantilever spring is further deflected in said first direction.

12. An apparatus for selectively retaining a needle sheath comprising:
   housing means; and
   engaging means interconnected with said housing for selectively engaging said sheath, wherein said engaging means comprises resilient means and a seat member, wherein said resilient means bears against a portion of said seat member when the apparatus is not in use, and wherein said resilient means is deflected to bear against a limited portion of said sheath positioned between said resilient means and said seat member during use of the apparatus.

13. An apparatus for selectively retaining a needle sheath comprising:
housing means; and
engaging means interconnected with said housing means for selectively retaining a sheath wherein said engaging means comprises a seat member having at least one V-shaped support portion for engaging said sheath; and
controlling means, for permitting a user to selectively control retaining engagement of said engaging means and said sheath.

14. An apparatus for selectively retaining a needle sheath comprising:
a housing;
retaining means interconnected with said housing for selectively engaging and retaining a sheath inserted into said housing, comprising:
resilient means; and,
support means positioned in opposing relationship to said resilient means wherein said sheath can be supported by said support means and retainingly engaged between said resilient means and said support means substantially intermediate of the ends of said sheath during use of said apparatus.

15. An apparatus for selectively retaining a needle sheath comprising:
a housing; and,
retaining means interconnected with said housing for selective retaining engagement and disengagement of a sheath in the substantial absence of simultaneous contact and relative movement between said retaining means and said sheath, said retaining means comprising a resilient member having a deflectable end for engaging said sheath and particularly adapted for griping a peripheral portion of said sheath to restrict both longitudinal, lateral and rotational movement of said sheath relative to said apparatus, and said retaining means further comprising a seat member in opposing relationship to said surface.

16. The apparatus of claim 14, wherein said seat means is positioned substantially entirely on one side of a plane centered about the longitudinal center axis defined by said opening.

17. The apparatus of claim 14, wherein said support means comprises two spaced support surfaces which each include a recess to receive said sheath and restrict lateral movement during use.

18. The apparatus of claim 17 wherein said resilient means laterally engages said sheath in a region substantially between said two support surfaces.

* * * * *